US012685481B2

(12) United States Patent
Shin et al.

(10) Patent No.: US 12,685,481 B2
(45) Date of Patent: Jul. 21, 2026

(54) APPARATUS FOR MANAGING ATOPIC DERMATITIS BASED ON LEARNING MODEL AND METHOD THEREFOR

(71) Applicant: EVERTRI, Seoul (KR)

(72) Inventors: Jae Yong Shin, Seoul (KR); Joo Young Oh, Seoul (KR); Sang Eun Lee, Seoul (KR)

(73) Assignee: EVERTRI, Seoul (KR)

( * ) Notice: Subject to any disclaimer, the term of this patent is extended or adjusted under 35 U.S.C. 154(b) by 851 days.

(21) Appl. No.: 17/927,760

(22) PCT Filed: May 26, 2021

(86) PCT No.: PCT/KR2021/006550
§ 371 (c)(1),
(2) Date: Jun. 26, 2023

(87) PCT Pub. No.: WO2021/242010
PCT Pub. Date: Dec. 2, 2021

(65) Prior Publication Data
US 2023/0320653 A1 Oct. 12, 2023

(30) Foreign Application Priority Data
May 29, 2020 (KR) ........................ 10-2020-0065426

(51) Int. Cl.
*A61B 5/00* (2006.01)
*G16H 50/20* (2018.01)
(52) U.S. Cl.
CPC .............. *A61B 5/445* (2013.01); *A61B 5/486* (2013.01); *A61B 5/7267* (2013.01); *A61B 5/7275* (2013.01); *G16H 50/20* (2018.01)
(58) Field of Classification Search
CPC ....... A61B 5/445; A61B 5/486; A61B 5/7267; A61B 5/7275; A61B 5/14546;
(Continued)

(56) References Cited

U.S. PATENT DOCUMENTS

2011/0295782 A1 12/2011 Stojadinovic et al.
2017/0103174 A1 4/2017 Kim et al.
(Continued)

FOREIGN PATENT DOCUMENTS

KR 10-2017-0023770 A 3/2017
KR 101864614 B1 * 6/2018
(Continued)

OTHER PUBLICATIONS

Impact of Weather Conditions on Atopic Dermatitis Prevalence in Abuja, Nigeria—Ibekwe et al. (Year: 2018).*
(Continued)

*Primary Examiner* — Patrick Fernandes
*Assistant Examiner* — Shawn Curtis Broughton
(74) *Attorney, Agent, or Firm* — Revolution IP, PLLC

(57) ABSTRACT

The present invention provides an apparatus for managing atopic dermatitis based on a learning model and a method therefor. The method for managing atopic dermatitis according to the present invention includes the steps of: collecting, basic data including a patient's daily life factor, biometric factor, mental health factor, skin status factor, weather-related environmental factor, and an atopic dermatitis severity index based on the medical record; learning a weight for each detailed variable by applying, to a learning model, the relationship between the atopic dermatitis severity index and respective detailed variables for a plurality of factors; determining a reference value of the weight for selecting, as valid variables, N detailed variables for each factor; reconstructing the learning model by selecting, for each factor, N valid variables; and predicting the atopic dermatitis severity index by applying, to the reconstructed learning model, the currently corrected basic data of the patient to be analyzed.

8 Claims, 6 Drawing Sheets

(58) Field of Classification Search

CPC ......... A61B 5/165; A61B 5/746; A61B 5/411;
A61B 5/7465; G16H 50/20; G16H 50/30;
G16H 50/70; G16H 10/60; G16H 15/00;
G06Q 10/05; G06Q 50/10; G06Q 50/20

See application file for complete search history.

(56) References Cited

U.S. PATENT DOCUMENTS

| | | | | |
|---|---|---|---|---|
| 2019/0136298 A1* | 5/2019 | Apte | ...................... | G16H 50/20 |
| 2019/0172587 A1 | 6/2019 | Park et al. | | |
| 2020/0110992 A1* | 4/2020 | Hosseinzadeh | ........ | G06N 3/094 |
| 2021/0052672 A1* | 2/2021 | Whitlock | ............. | A61K 9/0031 |

FOREIGN PATENT DOCUMENTS

| | | |
|---|---|---|
| KR | 10-2018-0079208 A | 7/2018 |
| KR | 10-2019-0083928 A | 7/2019 |
| KR | 10-2020-0054484 A | 5/2020 |

OTHER PUBLICATIONS

International Search Report for PCT/KR2021/006550 mailed Sep. 1, 2021 from Korean Intellectual Property Office.

* cited by examiner

[FIG. 1]
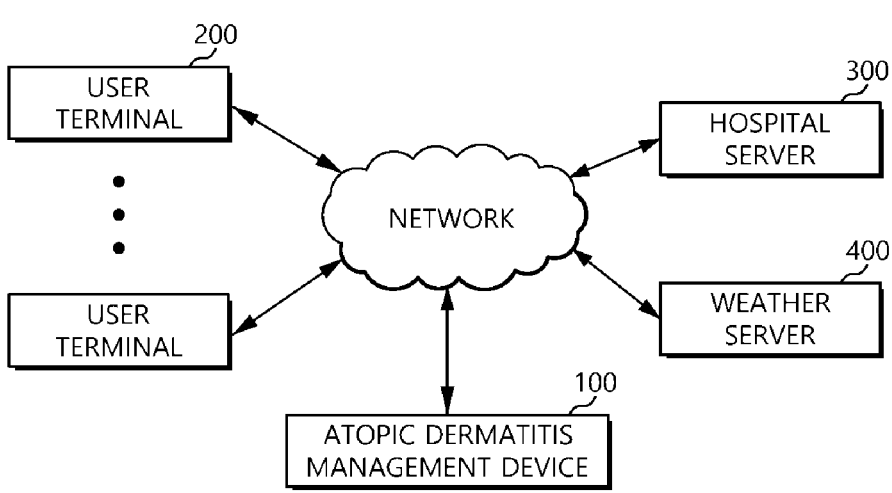
[FIG. 2]
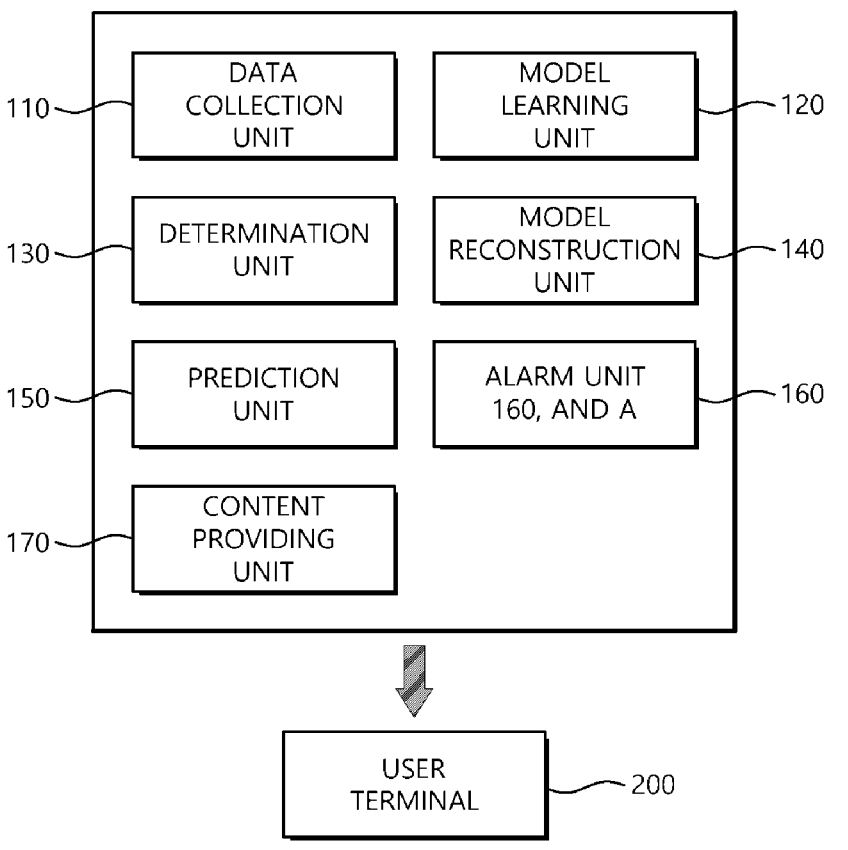

[FIG. 3]
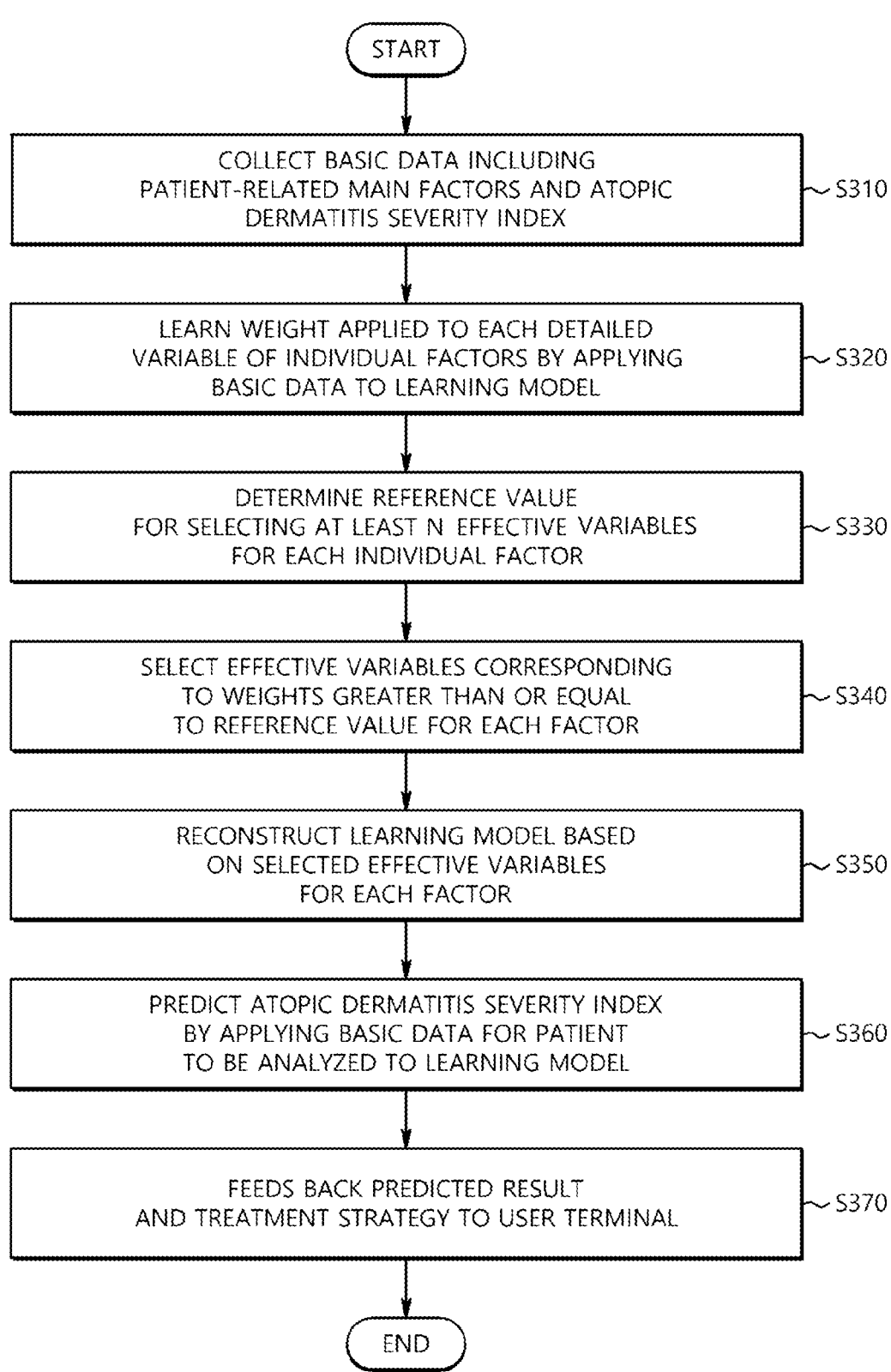

[FIG. 4]
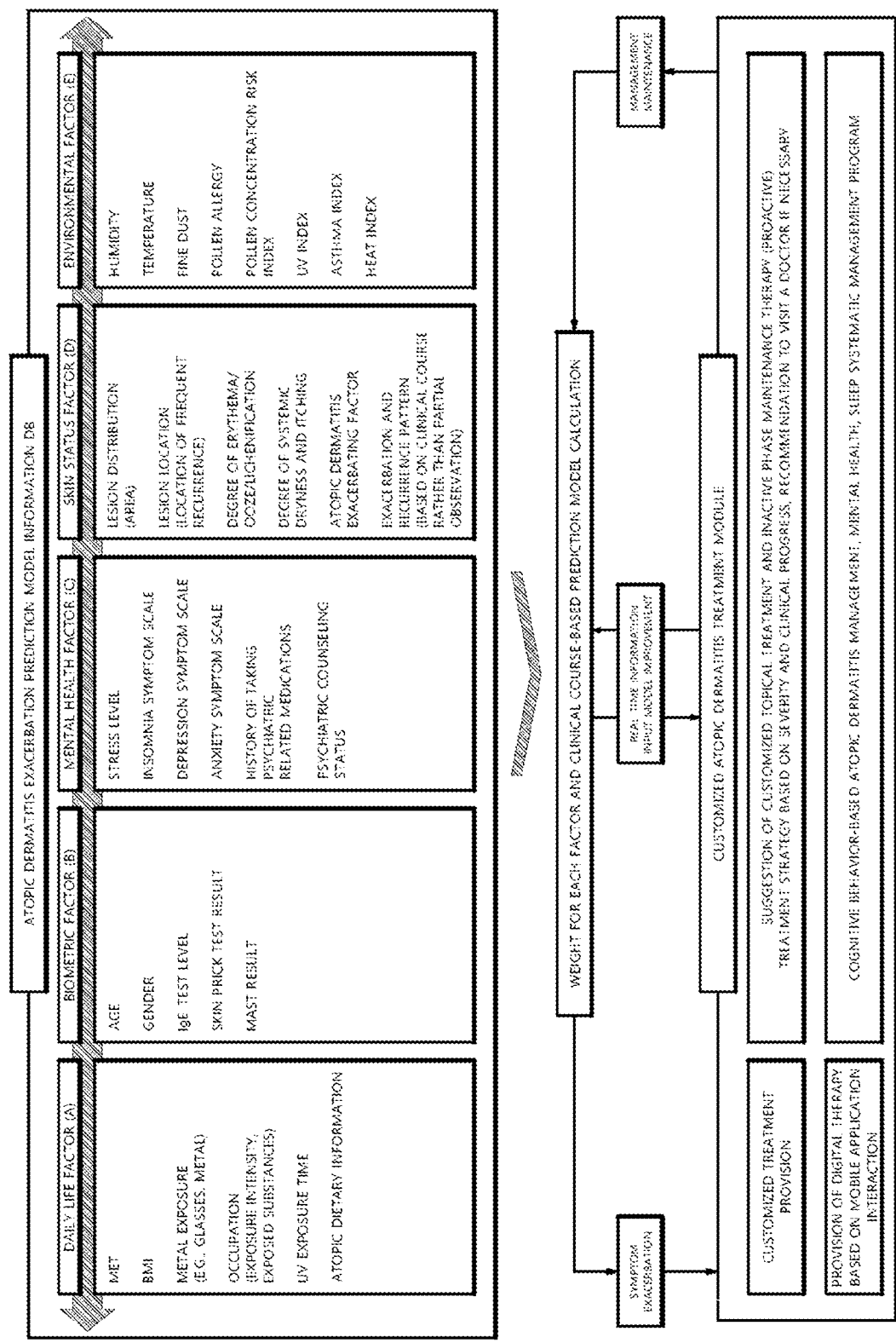

[FIG. 5]

| | SESSION TITLE | TRAINING CONTENT |
|---|---|---|
| 1 | HOW TO TAKE A BATH? | TRANSMISSION OF CORRECT KNOWLEDGE ABOUT BATHING AND MONITORING OF HABIT IMPROVEMENT |
| 2 | CHOOSING RIGHT MOISTURIZER FOR YOU | EDUCATION ON USE AND NECESSITY OF RIGHT MOISTURIZER FOR EACH SEASON AND SKIN TYPE<br><br>MONITORING CONTINUED USE OF MOISTURIZERS |
| 3 | SKIN BARRIER AND ATOPIC DERMATITIS | UNDERSTANDING PATHOPHYSIOLOGY OF INTESTINAL WALL<br><br>UNDERSTANDING IMPORTANCE OF TOPICAL TREATMENT |
| 4 | TOPICAL TREATMENT OF ATOPIC DERMATITIS | CORRECT DOSAGE AND USAGE ACCORDING TO SEVERITY OF SYMPTOMS AND EXTENT OF INVASION |
| 5 | SYSTEMIC TREATMENT OF ATOPIC DERMATITIS | IMPORTANCE OF EARLY SYSTEMIC TREATMENT<br><br>REDUCTION OF REJECTION THROUGH EDUCATION ON SIDE EFFECTS |
| 6 | WHAT TO EAT? | PREVENTION OF EXCESSIVE FOOD AVOIDANCE STRATEGIES |
| 7 | DUES STRATEGY FOR YOU | SUGGESTION OF CUSTOMIZED AGGRAVATING FACTOR AVOIDANCE METHOD |

COGNITIVE CORRECTION RELATED EDUCATION PROGRAM (EXAMPLE)

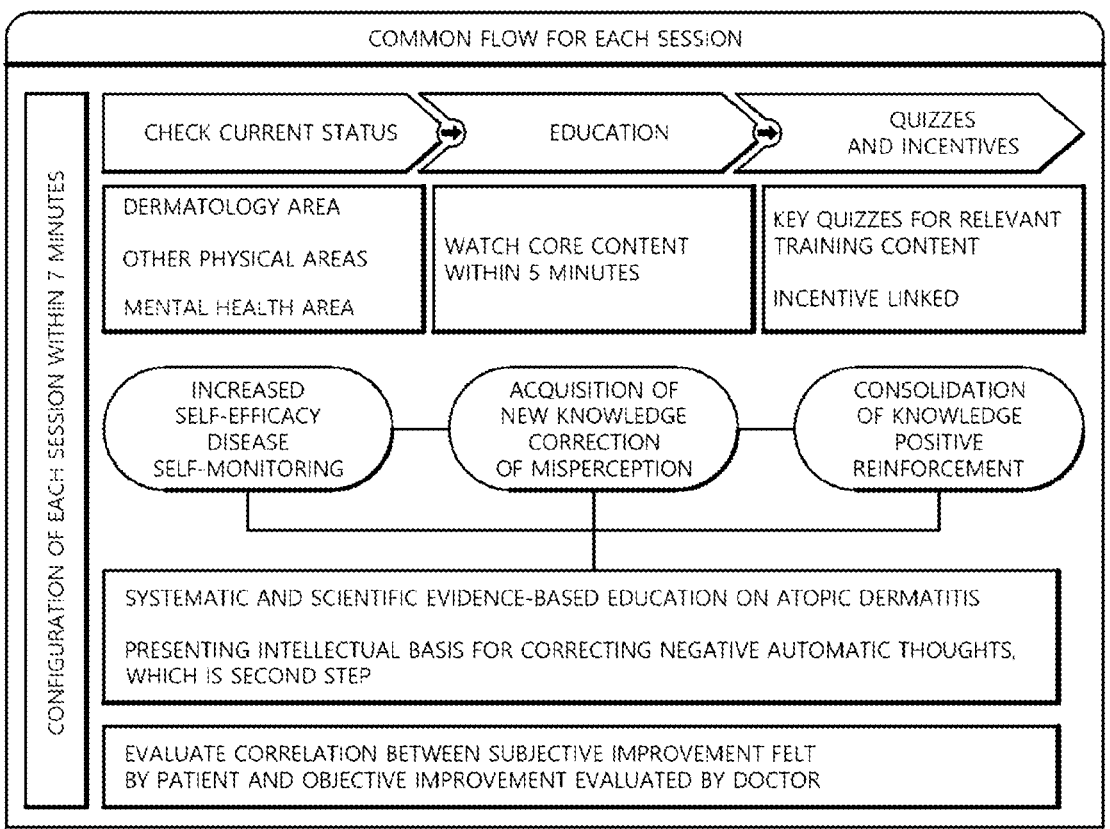

COMMON FLOW FOR EACH SESSION

CHECK CURRENT STATUS → EDUCATION → QUIZZES AND INCENTIVES

DERMATOLOGY AREA

OTHER PHYSICAL AREAS

MENTAL HEALTH AREA

WATCH CORE CONTENT WITHIN 5 MINUTES

KEY QUIZZES FOR RELEVANT TRAINING CONTENT

INCENTIVE LINKED

INCREASED SELF-EFFICACY DISEASE SELF-MONITORING

ACQUISITION OF NEW KNOWLEDGE CORRECTION OF MISPERCEPTION

CONSOLIDATION OF KNOWLEDGE POSITIVE REINFORCEMENT

SYSTEMATIC AND SCIENTIFIC EVIDENCE-BASED EDUCATION ON ATOPIC DERMATITIS

PRESENTING INTELLECTUAL BASIS FOR CORRECTING NEGATIVE AUTOMATIC THOUGHTS, WHICH IS SECOND STEP

EVALUATE CORRELATION BETWEEN SUBJECTIVE IMPROVEMENT FELT BY PATIENT AND OBJECTIVE IMPROVEMENT EVALUATED BY DOCTOR

CONFIGURATION OF EACH SESSION WITHIN 7 MINUTES

[FIG. 6]

| AUTOMATIC THOUGHT IMPROVEMENT PROGRAM (EXAMPLE) | |
|---|---|
| DETAILED SESSIONS (2 SESSIONS EACH) | AUTOMATIC THOUGHT IMPROVEMENT TRAINING CONTENT |
| LET'S TRAIN TO OVERCOME INSOMNIA | EXPLAIN JUSTIFICATION FOR SLEEP DISORDERS<br><br>METHOD TO SYSTEMATICALLY MANAGE INSOMNIA ACCOMPANYING ATOPIC DERMATITIS, INCLUDING COGNITIVE CORRECTION RELATED TO INSOMNIA |
| DOES ATOPIC DERMATITIS HAVE TO BE DEPRESSED? | EDUCATION ON THE COGNITIVE TRIAD OF DEPRESS<br><br>METHODS FOR MANAGING AND CONTROLLING DEPRESSIVE SYMPTOMS ACCOMPANYING ATOPIC DERMATITIS |
| SHOULD I BE ANXIOUS OUTSIDE? | UNDERSTANDING OVERESTIMATION, CATASTROPHIC THINKING, AVOIDANCE BEHAVIOR, SAFETY BEHAVIOR, ETC. RELATED TO SOCIAL ANXIETY SYMPTOMS ACCOMPANYING ATOPIC DERMATITIS |
| DO EXPOSURE AND REACTION PREVENTION TRAINING. | EDUCATION ON REDUCING AVOIDANCE BEHAVIOR RELATED TO SYMPTOMS OF ATOPIC DERMATITIS, EXPOSURE TO SYMPTOM-CAUSING SITUATIONS, AND PREVENTION OF FALSE REACTIONS FOR TEMPORARY RELIEF OF SYMPTOMS |

AUTOMATIC THOUGHT IMPROVEMENT PROCESS

LET'S TRAIN TO OVERCOME INSOMNIA (EXAMPLE)

- INTRODUCTION TO COMMON COGNITIVE DISTORTIONS OF INSOMNIA (ORIENTATION)

IF I DON'T GET 8 HOURS OF SLEEP TODAY, I WON'T BE ABLE TO DO ANYTHING TOMORROW.

IF I DOZE OFF TOMORROW, I'LL BE SEEN AS INCOMPETENT AT WORK.

IT CAN BE ITCHY WHILE SLEEPING, SO I SHOULD GO TO BED AS LATE AS POSSIBLE.

- IDENTIFY ERRORS IN PAST EXPERIENCES AND IDENTIFY KEY COGNITIVE DISTORTIONS IN INDIVIDUALS

OVERGENERALIZATION OF PAST EXPERIENCE

IDENTIFICATION OF AUTOMATIC THOUGHTS BASED ON COMMON COGNITIVE DISTORTIONS ABOUT UNEXPERIENCED EVENTS

- REVIEW REAL LIFE THROUGH ASSIGNMENTS, DRAW RATIONAL RESPONSES, RECORD CHANGED THOUGHTS

WHEN YOU DIDN'T GET ENOUGH SLEEP, WERE YOU REALLY INCAPABLE OF DOING ANYTHING? (FOR EXAMPLE, TEST)

DID MY BOSS THINK I WAS INCOMPETENT? (FOR EXAMPLE, TO WHAT EXTENT ARE YOU INCOMPETENT?)

HOW MANY DAYS HAVE YOU HAD AN ITCHY NIGHT IN YOUR SLEEP? (FOR EXAMPLE, HOW MANY TIMES HAVE YOU ACTUALLY WOKEN UP FROM ITCHING?)

[FIG. 7]

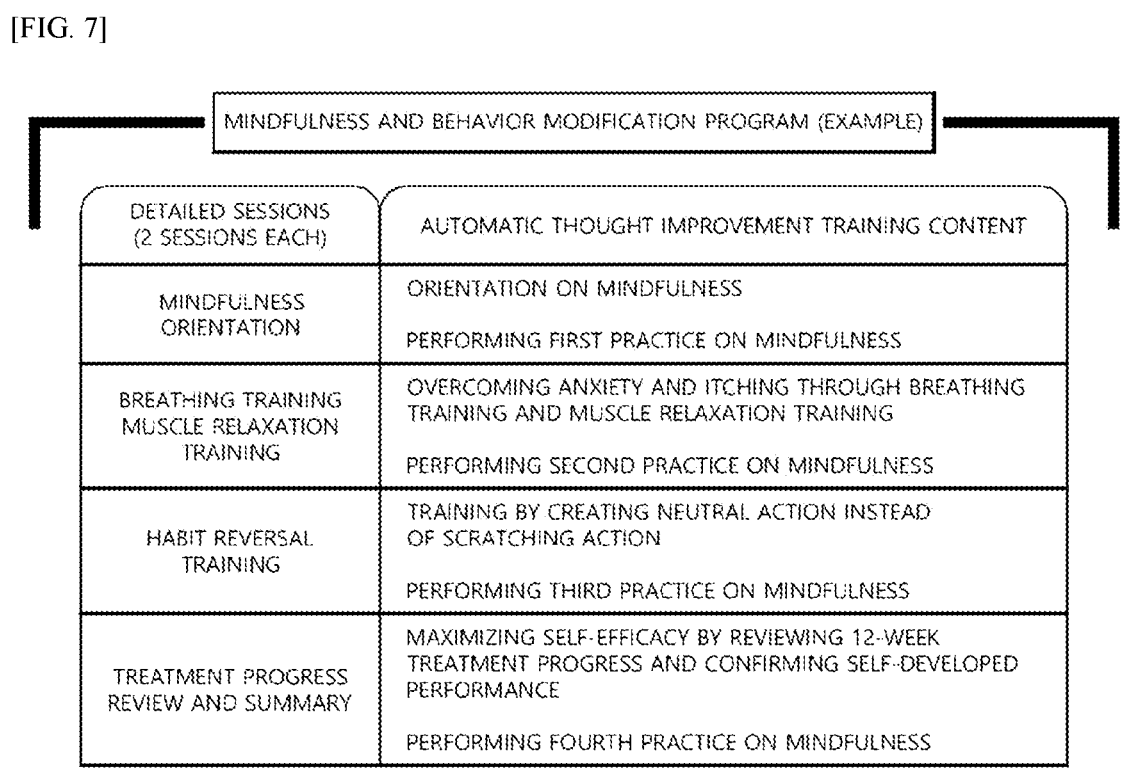

| MINDFULNESS AND BEHAVIOR MODIFICATION PROGRAM (EXAMPLE) | |
|---|---|
| DETAILED SESSIONS (2 SESSIONS EACH) | AUTOMATIC THOUGHT IMPROVEMENT TRAINING CONTENT |
| MINDFULNESS ORIENTATION | ORIENTATION ON MINDFULNESS<br><br>PERFORMING FIRST PRACTICE ON MINDFULNESS |
| BREATHING TRAINING MUSCLE RELAXATION TRAINING | OVERCOMING ANXIETY AND ITCHING THROUGH BREATHING TRAINING AND MUSCLE RELAXATION TRAINING<br><br>PERFORMING SECOND PRACTICE ON MINDFULNESS |
| HABIT REVERSAL TRAINING | TRAINING BY CREATING NEUTRAL ACTION INSTEAD OF SCRATCHING ACTION<br><br>PERFORMING THIRD PRACTICE ON MINDFULNESS |
| TREATMENT PROGRESS REVIEW AND SUMMARY | MAXIMIZING SELF-EFFICACY BY REVIEWING 12-WEEK TREATMENT PROGRESS AND CONFIRMING SELF-DEVELOPED PERFORMANCE<br><br>PERFORMING FOURTH PRACTICE ON MINDFULNESS |

APPARATUS FOR MANAGING ATOPIC DERMATITIS BASED ON LEARNING MODEL AND METHOD THEREFOR

CROSS REFERENCE TO PRIOR APPLICATIONS

This application is the 35 U.S.C. 371 national stage of international application PCT/KR2021/006550 filed on May 26, 2021 which claims priority to Korean Patent Application No. 10-2020-0065426 filed on May 29, 2020. The entire contents of each of the above-identified applications are hereby incorporated by reference.

TECHNICAL FIELD

The present invention relates to an apparatus for managing atopic dermatitis based on a learning model and a method therefor, and more particularly, to an apparatus for managing atopic dermatitis based on a learning model and a method therefor, which are capable of predicting and providing an atopic status based on basic data collected for a patient.

BACKGROUND ART

Atopic dermatitis is an inflammatory disease of an immune system accompanied by eczematous lesions and chronic itching in specific areas according to age. Although discussed according to epidemiological studies, there are reports that 10-20% of patients in school age have atopic dermatitis symptoms. Even in adulthood, 10% of atopic patients progress to adult atopic dermatitis in which lesions persist, itching persists, and the skin becomes lichenified.

Atopic dermatitis repeatedly worsens and improves, adversely affecting the quality of life of patients. As a result of a perception survey on the quality of life of patients with severe atopic dermatitis, targeting 155 ordinary people over 19 and under 60 in Korea, it has been reported that the quality of life of patients with severe atopic dermatitis is at the level of hearing and visual impairment, and patients with severe atopic dermatitis suffer from sleep disturbance due to itching for an average of 4 days a week.

63% of critically ill patients experience itching that lasts for more than 12 hours, and respondents answered that they would live 3.8 years in good health and give up 6.2 years of life rather than living 10 years as untreated severe atopic dermatitis patients. This figure is similar to a result of analyzing the reduction in life expectancy according to the quality of life of the hearing or visually impaired (3.9 years). On the other hand, respondents answered that they would give up about 1.5 years of life if the treatment went well, so it seems that the response to life expectancy varies greatly depending on whether the treatment is effective. From this, it was confirmed that the desire for atopic dermatitis treatment was indirectly very strong.

Decreased quality of life is linked to psychiatric symptoms of patients with atopic dermatitis, and since patients with atopic dermatitis repeat improvement and worsening of symptoms, a system that allows immediate medical attention from a specialist should be established when necessary.

A recent hot topic in the health care system is establishing policies that maximize value. Here, value is a factor that considers both the amount of input resources and the produced health outcomes, and if the same result is obtained, it means that a high quality level of health is achieved with preventive treatment and minimal resource input. Therefore, a value-based medical management platform that prevents the severity of atopic patients from going to moderate levels and prepares a method for self-control of symptoms is required.

The background technology of the present invention is disclosed in Korean Patent Laid-Open No. 2019-0083928 (published on Jul. 15, 2019).

DISCLOSURE

Technical Problem

The present invention aims to provide an apparatus for managing atopic dermatitis based on a learning model and a method therefor, which are capable of predicting deterioration of atopic dermatitis condition by applying basic data collected for a patient to a pre-learned learning model.

Technical Solution

The present invention provides a method for managing atopic dermatitis by using an apparatus for managing atopic dermatitis, the method including the steps of: collecting, by the hour, basic data including a patient's daily life factor, biometric factor, mental health factor, skin status factor, weather-related environmental factor, and an atopic dermatitis severity index based on the patient's medical record; learning a weight for each detailed variable by applying, to a learning model, the relationship between the atopic dermatitis severity index and respective detailed variables for a plurality of factors; determining a reference value of the weight for selecting, as valid variables, at least N detailed variables (wherein N is an integer greater than or equal to 2) for each factor; reconstructing the learning model by selecting, for each factor, the at least N valid variables corresponding to the weight that is greater than or equal to the reference value; and predicting the atopic dermatitis severity index by applying, to the reconstructed learning model, the currently corrected basic data of the patient to be analyzed.

In addition, the step of learning the weight for each detailed variable may include performing learning by applying, to the learning model, detailed variables for each factor for the patient collected at a first time and atopic dermatitis severity index of the patient collected at a second time when T1 time has elapsed from the first time.

In addition, the step of predicting may include applying the effective variables for each factor among basic data collected for the patient to be analyzed at the current time to the pre-learned learning model, so as to predict a future atopic dermatitis severity index of the patient to be analyzed at a future time when T1 time has elapsed from the current time.

The method may further include feeding back a treatment strategy for at least one of a customized topical application, a maintenance therapy, and a recommendation to visit a hospital, which correspond to the predicted result, to a user terminal of the corresponding patient along with the predicted result.

The basic data may be collected through a user terminal corresponding to the patient, a hospital server storing medical information of the patient, and a weather server providing location-based weather information.

In addition, the method may further include providing a plurality of educational content for improving atopic dermatitis improvement step by step through a user terminal of the patient for the patient from whom the basic data is collected, wherein the educational content includes cognitive correction content which is an educational program that corrects the patient's false perception of atopic dermatitis by providing basic knowledge related to atopic dermatitis during a set period, automatic thought improvement content which is an educational program that is provided during a set period after completion of the cognitive correction content and improves negative thinking that negatively affects daily life and disease progress based on questionnaires and responses presented to patients, and behavioral correction content which is an educational program that is provided during a set period after completion of the automatic thought improvement content and is provided for meditation education and training for the patient's mindfulness.

The present invention provides an apparatus for managing atopic dermatitis, the apparatus including: a data collection unit which collects, by the hour, basic data including a patient's daily life factor, biometric factor, mental health factor, skin status factor, weather-related environmental factor, and an atopic dermatitis severity index based on the patient's medical record; a model learning unit which learns a weight for each detailed variable by applying, to a learning model, the relationship between the atopic dermatitis severity index and respective detailed variables for a plurality of factors; a determination unit which determines a reference value of the weight for selecting, as valid variables, at least N detailed variables (wherein N is an integer greater than or equal to 2) for each factor; a model reconstruction unit which reconstructs the learning model by selecting, for each factor, the at least N valid variables corresponding to the weight that is greater than or equal to the reference value; and a prediction unit which predicts the atopic dermatitis severity index by applying, to the reconstructed learning model, the currently corrected basic data of the patient to be analyzed.

In addition, the model learning unit may perform learning by applying, to the learning model, detailed variables for each factor for the patient collected at a first time and atopic dermatitis severity index of the patient collected at a second time when T1 time has elapsed from the first time.

In addition, the prediction unit may apply the effective variables for each factor among basic data collected for the patient to be analyzed at the current time to the pre-learned learning model, so as to predict a future atopic dermatitis severity index of the patient to be analyzed at a future time when T1 time has elapsed from the current time.

In addition, the apparatus may further include an alarm unit which feeds back a treatment strategy for at least one of a customized topical application, a maintenance therapy, and a recommendation to visit a hospital, which correspond to the predicted result, to a user terminal of the corresponding patient along with the predicted result.

In addition, the apparatus may further include a content providing unit which provides a plurality of educational content for improving atopic dermatitis improvement step by step through a user terminal of the patient for the patient from whom the basic data is collected, wherein the educational content includes cognitive correction content which is an educational program that corrects the patient's false perception of atopic dermatitis by providing basic knowledge related to atopic dermatitis during a set period, automatic thought improvement content which is an educational program that is provided during a set period after completion of the cognitive correction content and improves negative thinking that negatively affects daily life and disease progress based on questionnaires and responses presented to patients, and behavioral correction content which is an educational program that is provided during a set period after completion of the automatic thought improvement content and is provided for meditation education and training for the patient's mindfulness.

Advantageous Effects

According to the present invention, it is possible to provide an advantage of predicting and managing exacerbation of atopic dermatitis condition by applying basic data collected for a patient to a pre-learned learning model, and suggesting a customized treatment strategy based on the prediction results.

In addition, according to the present invention, by providing an atopic dermatitis management platform based on mobile application interaction for cognitive behavior-based atopic management, mental health management, and stress management, it is possible to induce symptom improvement and prevention of exacerbation of atopic dermatitis and contribute to improving the quality of life of atopic patients.

DESCRIPTION OF DRAWINGS

FIG. 1 is a diagram illustrating a system for managing atopic dermatitis according to an embodiment of the present invention.

FIG. 2 is a diagram illustrating the configuration of the system for managing atopic dermatitis illustrated in FIG. 1.

FIG. 3 is a diagram for describing a method for managing atopic dermatitis using FIG. 2.

FIG. 4 is a diagram for describing an application principle of a learning model according to an embodiment of the present invention.

FIG. 5 is a diagram for describing cognitive correction content according to an embodiment of the present invention.

FIG. 6 is a diagram for describing automatic thought improvement content according to an embodiment of the present invention.

FIG. 7 is a diagram for describing behavior correction content according to an embodiment of the present invention.

BEST MODE FOR CARRYING OUT THE INVENTION

Hereinafter, embodiments of the present invention will be described in detail with reference to the accompanying drawings, so that those of ordinary skill in the art to which the present invention belongs may easily carry out the present invention. However, the present invention may be implemented in various different forms and is not limited to the embodiments described herein. In order to clearly explain the present invention, parts irrelevant to the description are omitted in the drawings, and similar reference numerals are assigned to similar parts throughout the specification.

It will be understood that when a portion is referred to as being "connected to" another portion, it may be "directly connected to" the other portion or "electrically connected to" the other portion with intervening portions therebetween. It will be understood that the terms "comprise," "include," or "have" as used herein specify the presence of stated elements, but do not preclude the presence or addition of one or more other elements.

FIG. 1 is a diagram illustrating a system for managing atopic dermatitis according to an embodiment of the present invention.

Referring to FIG. 1, the system for managing atopic dermatitis according to an embodiment of the present invention may include an atopic dermatitis management device 100, a user terminal 200, a hospital server 300, and a weather server 400, which may be communicatively connected to each other through wired and wireless networks and transmit and receive information with each other.

Hereinafter, a wireless network is mainly described as an example, but a wireless network, a wired network, or a wired/wireless combined network may be used. The wireless network may include at least one of RF, WLAN, Wi-Fi, and Bluetooth schemes, and various known wireless network schemes may be used.

The atopic dermatitis management device 100 may be a server itself for atopic dermatitis management, or may be an application implemented as software on a device such as the user terminal 200. The server or the application may provide a corresponding service to authenticated users through member registration or input of personal information. The user terminal 200 may provide related services by being connected to the atopic dermatitis management device 100 through a network while the application is running.

The user terminal 200 may refer to a device capable of exchanging information by accessing a network, such as a PC, a tablet, a notebook, a pad, or a smart phone. Here, in the case of a device having a built-in wireless function (a smart phone, a laptop, a pad, etc.), the function provided by the device 100 of the present invention may be provided in the form of a mobile application on the device.

Here, the user terminal 200 may correspond to a patient-side terminal, or may correspond to a medical personnel-side terminal belonging to a medical institution such as a hospital. In the latter case, when a patient visits a hospital, a medical personnel can execute a process related to an atopic dermatitis management service on behalf of the patient and perform diagnosis, consultation, prescription, treatment, and prognosis management according to the result.

The hospital server 300 may manage medical information (medical information DB) including the patient's personal information (age, gender, etc.), medical records for the past several months, a variety of examination information, prescription information, atopic severity index, and the like. Here, a variety of examination information may include an allergy level (IgE test level), a skin prick test result, a multiple allergen simultaneous test (MAST) result, and the like.

The hospital server 300 may provide biometric information factors of the patient, including the age, the gender, the IgE level, the skin prick test result, and the MAST result of the patient.

In addition, the hospital server 300 may continuously monitors medical records, prescription details, and incurred medical expenses based on dermatologist treatment as major monitoring indicators based on the medical information DB, and may manage a history of symptom exacerbation, systemic drug use, topical drug use, strength of each drug, dose, medication compliance, continuous outpatient visit rate, moisturizer prescription, severity, and the like.

The hospital server 300 may operate in conjunction with or include an electronic medical record (EMR), an order communication system (OCS), and a picture archiving and communication system (PACS). Based on this, the hospital server 300 may collect, integrate and manage a variety of information related to patients and may match and manage related information for each patient.

The weather server 400 provides weather information based on location information (GPS). The weather server 400 may provide weather-related environmental factors including humidity, temperature, fine dust, pollen allergy, pollen concentration risk index, UV index, asthma index, heat index, and the like in response to the user's location.

The user terminal 200 receives basic information registered from the patient while the mobile application is running and transmits the basic information to the atopic dermatitis management device 100. In this case, the basic information includes a daily life factor, mental health factor, and skin status factor related to the patient, and is included in the patient's basic examination data.

Here, the daily life factor may include a metabolic equivalent of task (MET), a body mass index (BMI), a metal exposure (e.g. glasses, metal), occupation (exposed substances, exposure intensity), UV exposure time, atopic dietary information, and the like. The mental health factor may include the patient's stress level, insomnia symptom scale, depression symptom scale, anxiety symptom scale, history of taking psychiatric related medications, psychiatric counseling status, and the like. The skin status factor may include lesion distribution (area), lesion location (location of frequent recurrence), degree of erythema/ooze/lichenification, degree of systemic dryness and itching, atopic dermatitis exacerbating factor, exacerbation and recurrence pattern (based on clinical course), and the like.

The mobile application that is executed on the user terminal 200 may provide a menu for inputting the above-described basic information, and may provide functions such as survey, question and answer, and photo taking for the user's information input convenience.

The user terminal 200 may receive basic information at the start of a corresponding application session twice a week or at any time, and may provide a pop-up notification prompting information input. In addition, when basic information is input, self-assessment data may be input within two minutes by dividing it into a skin health area and a mental health area.

FIG. 2 is a diagram illustrating the configuration of the atopic dermatitis management device illustrated in FIG. 1, and FIG. 3 is a diagram for describing a method for managing atopic dermatitis using FIG. 2.

Referring to FIGS. 2 and 3, the atopic dermatitis management device 100 according to an embodiment of the present invention includes a data collection unit 110, a model learning unit 120, a determination unit 130, a model reconstruction unit 140, a prediction unit 150, an alarm unit 160, and a content providing unit 170.

First, the data collection unit 110 may collect, by the time, basic data including a patient's daily life factor (A), biometric factor (B), mental health factor (C), skin status factor (D), weather-related environmental factor (E), and an atopic dermatitis severity index based on the patient's medical record (S310).

The data collection unit 110 may construct big data by collecting basic data on a plurality of patients over time.

The data collection unit 110 may collect the patient's basic data from the user terminal 200 corresponding to the patient, the hospital server 300 managing medical information of the patient, and the weather server 400 providing location-based weather information.

For example, the factors related to A, C, and D may be collected from the user terminal 200, the factors related to B and the atopic dermatitis severity index may be collected from the hospital server 300, and the factors related to E may be collected from the weather server 400. Here, in the case of the factors related to E, environment-related data corresponding to the current location (current GPS location, residence on personal information, etc.) may be called by communicating with the weather server 400 on the mobile application executed on the terminal.

Next, detailed variables for each major factor will be described in detail with reference to FIG. 4.

FIG. 4 is a diagram for describing an application principle of a learning model according to an embodiment of the present invention.

As illustrated in FIG. 4, the daily life factor (A) includes MET, BMI, metal exposure, occupation, UV exposure time, atopic dietary information, and the like. The biometric factor (B) includes the patient's age, sex, IgE level, skin prick test result, multiple allergen simultaneous test result, and the like.

The mental health factor (C) includes the patient's stress level, insomnia symptom scale, depression symptom scale, anxiety symptom scale, history of taking psychiatric medications, psychiatric counseling, and the like. The skin status factor (D) includes lesion distribution, lesion location, degree of erythema/ooze/lichenification, degree of systemic dryness and itching, atopic dermatitis exacerbation factor, exacerbation and recurrence pattern, and the like. The weather-related environmental factor (E) includes humidity, temperature, fine dust, pollen concentration risk index, UV index, asthma index, heat index, and the like.

Detailed variables for each factor collected for patients and the corresponding atopic dermatitis severity index are used for learning of the learning model.

To this end, the model learning unit 120 learns the weight applied to each detailed variable by applying the relationship between the detailed variables included in each factor from A to E and the corresponding atopic dermatitis severity index to the learning model (S320).

In the case of FIG. 4, there are five types of factors, and a total of about 30 types of detailed elements of each factor exist. Therefore, the model learning unit 120 learns the weight of each variable by using about 30 detailed variables collected for patients.

Here, learning may be performed by using the learning model of Equation 1 below.

$$Y = \omega_0 + \omega_1 X_1 + \ldots + \omega_p X_p + \epsilon \qquad \text{[Equation 1]}$$

where $X_i$ represents the i-th variable, $\omega_i$ represents the i-th weight (coefficient) applied to the i-th variable, $\epsilon$ represents the error correction coefficient between the atopic index (Y) predicted through the model of Equation 1 and the patient's actual atopic dermatitis severity index. $\epsilon$ is an error/residual and is a correction value for correcting this with the difference between the predicted Y and the actual atopic dermatitis severity index.

In Equation 1, i is an index of a variable, $i=1, \ldots, p\}$. In this case, p corresponds to the type (number) of variables used in learning. In the case of an embodiment of the present invention, p=30.

The model learning unit 120 estimates the weight $\omega$ for each variable by machine learning analysis of the relationship between the 30 independent variables collected for patients and the predicted Y value corresponding thereto.

That is, the model learning unit 120 learns the model according to Equation 1 by using the 30 independent variables collected for patients and the actual atopic dermatitis severity index corresponding thereto. At this time, the model learning unit 120 may finally determine the value of the weight $\omega_i$ by adjusting and iteratively learning each weight value until the error $\epsilon$ falls below a set threshold.

Here, using the learning model of Equation 1, the current atopic dermatitis severity index may be predicted in response to the currently collected data of the patient to be analyzed, but the atopic dermatitis severity index after a set period of time (e.g., 1 week later) may be predicted in response to the currently collected data.

In the former case, when learning the model, it is sufficient to perform learning by using the patient's main factors (30 variables) and severity indices collected at the same first time point as learning data. In the latter case, when learning the model, the patient's main factors (including 30 variables) collected at the first time point and the patient's atopic dermatitis severity index collected at the second time point having a lag therefrom may be used as learning data.

In the latter case, detailed variables for each factor for the patient collected at the first time by the model learning unit 120 and atopic dermatitis severity index observed at the second time when T1 time (e.g., 1 week) has elapsed from the first time for the same patient may be used as training data to learn the learning model.

As described above, depending on which point in time the Y value of the learning model is used, it may be divided into a first learning model for deriving an atopic dermatitis severity index at the current time and a second learning model for deriving a future severity index. Of course, by using both of these two learning models, the present severity index and the prediction result of the severity index after 1 week are provided together, so that deterioration or improvement from the present may be predicted in advance.

After the learning through step S320 is completed, the determination unit 130 determines a reference value of weights for selecting at least N detailed variables (N is an integer of 2 or more) for each individual factor as effective variables (S330).

According to the previous model learning, p weights (Wi; i=1–p) are derived corresponding to p variables. Here, a variable having a low weight corresponds to a variable having a low importance in the learning model. However, all of the factors A to E correspond to the necessary factors, and thus, in the present embodiment, a threshold value is determined so that at least N (e.g., 3) detailed variables for each factor may be reflected in the learning model.

That is, the determination unit 130 determines a reference value (threshold value) for selecting at least three detailed variables for each factor as effective variables. Through the reference value, it is possible to take at least three variables for each factor as effective variables while excluding variables whose weights are smaller than the reference value.

Thereafter, the model reconstruction unit 140 selects at least N effective variables corresponding to the weights greater than or equal to the reference value for each factor by using the determined reference value (S340), and reconstructs the learning model based on the selected effective variables (S350).

That is, the model reconstruction unit 140 reconstructs the learning model only with significant variables (effective variables) whose weights are greater than or equal to the threshold value.

At this time, in step S340, at least three variables are selected for each factor according to the previously determined reference value. In the process, the number of variables selected for each factor may be equal to or different from each other.

For example, when there are four variables having weights greater than or equal to the reference value among six variables related to the factor A in FIG. 4, the four variables are selected as effective variables for the factor A, and when three of five variables related to the factor B have weights greater than or equal to the reference value, the three variables are selected as effective variables for the factor B. In addition, when there are five of six variables related to the factor C, the five variables are selected as effective variables for the factor C.

When the model of Equation 1 is reconstructed with the selected effective variables, the total number p of variables becomes smaller than 30 during learning. Therefore, p may be replaced by q, so that q<p.

The reason for restructuring the model in this way is to exclude variables with weights below the threshold from the list of variables necessary for prediction because they may be regarded as factors with little relevance to changes in atopic symptoms. Of course, through this model reconstruction, the model may be lightened and the computational efficiency and speed of the processor may be improved.

Here, in the case of the present invention, a process of additionally fine-tuning the weights of the effective variables by performing relearning on the model reconstructed with the effective variables may be included. That is, the reconstructed model may be relearned by applying the effective variable value corresponding to the patient and the atopic dermatitis severity index to the reconstructed model.

When the model is completed through reconstruction of the learning model, the atopic dermatitis severity index of the patient may be derived simply by applying the collected basic data for the patient to the corresponding learning model.

The prediction unit 150 predicts the atopic dermatitis severity index for the patient to be analyzed by applying the currently collected basic data (effective variables for the factors A to E) for the patient to be analyzed to the reconstructed learning model (S360).

That is, the prediction unit 150 derives and provides the atopic dermatitis severity index by substituting the effective variables for each factor collected for the patient to be analyzed at the current time as the value of each variable ($X_i$) in the learning model.

Here, as described above, according to the configuration of the model, the current atopic dermatitis severity index may be derived corresponding to the currently collected data of the patient to be analyzed, and the atopic dermatitis severity index after 1 week may be provided.

In the latter case, the prediction unit 150 may apply the effective variables for each factor collected for the patient to be analyzed at the current time to the learning model, so as to predict the future atopic dermatitis severity index of the patient subject to analysis at a future time when T1 time (e.g., 1 week) has elapsed from the current time. In addition, by comparing the predicted severity index with the current severity index of the patient, it is possible to determine whether the symptoms are worsening or improving.

Next, the alarm unit 160 feeds back and informs the predicted result and the corresponding treatment strategy (customized topical application agent, maintenance therapy, recommendation to visit a hospital, etc.) to the user terminal 200 of the corresponding patient (S370).

Here, when the user terminal 200 receives the corresponding alarm, the user terminal 200 may notify the corresponding information in the form of a pop-up or the like. Through this, the user terminal 200 may notify the prediction result of the condition and worsening symptoms of atopic dermatitis and guide a customized treatment strategy based on the prediction result.

In addition, the present invention may provide digital educational content that may help improve symptoms of atopic dermatitis.

To this end, the content providing unit 170 may provide a plurality of educational content for improving atopic dermatitis step by step through the user terminal of the patient for the patient from whom the basic data is collected. For example, when the basic data is received from the patient in the mobile application environment of the user terminal 200, the prediction result may be provided as feedback based on the basic data, or additional educational content may be provided.

The educational content may include cognitive correction content, automatic thought improvement content, and behavior correction content, each of which may include a training course of a set period (e.g., 4 weeks). The content providing unit 170 may sequentially provide the cognitive correction content (step 1), the automatic thought improvement content (step 2), and the behavioral correction content (step 3), and may provide the next level of educational content after completing the previous level of educational content.

FIG. 5 is a diagram for describing cognitive correction content according to an embodiment of the present invention.

As illustrated in FIG. 5, the cognitive correction content corresponds to an educational program that provides basic knowledge related to atopic dermatitis and corrects the patient's false perception of atopic dermatitis based on cognitive behavioral treatment. Here, individual training content are included in detail for each session. Each session may have a common flow and may include current status checking, education, quizzes, and incentive courses. Through this, new knowledge acquisition and false recognition may be improved.

FIG. 6 is a diagram for describing automatic thought improvement content according to an embodiment of the present invention.

As illustrated in FIG. 6, the automatic thought improvement content corresponds to an educational program that conducts training to improve negative thinking that negatively affects daily life and disease progress based on questionnaires and responses presented to patients. The automatic thought improvement program includes sections related to insomnia, depression, anxiety, exposure, and reaction prevention, and includes automatic thought improvement training for each session. In addition, through this, errors in past experiences are identified and orientation is provided for common cognitive distortions, thereby finding core cognitive distortions associated with negative automatic thoughts.

FIG. 7 is a diagram for describing behavior correction content according to an embodiment of the present invention.

As illustrated in FIG. 7, the behavior correction content corresponds to an educational program for meditation education and training for mindfulness of the patient in the last step. Through this mindfulness, while continuing to practice behavior correction, it is possible to manage stress through mindfulness meditation and training.

Since atopic dermatitis is a disease in which improvement and deterioration are repeated, stress management is essential, and stress caused by exacerbation of dermatitis has a vicious cycle of exacerbating the disease again. Therefore, for systematic management, mindfulness meditation education and training may be organized into several sessions and provided for 4 weeks. Mindfulness is a universally used method for stress management, and various versions of mindfulness, such as the acceptance model and the habit reversal, may be used in combination.

According to the present invention, it is possible to provide an advantage of predicting and managing exacerbation of atopic dermatitis condition by applying basic data collected for a patient to a pre-learned learning model, and suggesting a customized treatment strategy based on the prediction results.

In addition, according to the present invention, by additionally providing digital treatment content based on mobile application interaction, it enables cognitive behavior-based atopic dermatitis management, mental health management, and stress management, which may contribute to improving the quality of life of atopic patients as well as preventing worsening of symptoms and inducing improvement.

The present invention has been described with reference to the embodiments illustrated in the drawings, but this is only an example. It will be understood by those of ordinary skill in the art that various modifications and equivalents thereto may be made thereto. Accordingly, the true technical protection scope of the present invention should be defined by the technical spirit of the appended claims.

The invention claimed is:

1. A method for managing atopic dermatitis by using an apparatus for managing atopic dermatitis, the method comprising:

collecting, on an hourly basis, patient data for a patient, the patient data comprising daily life factor data, biometric factor data, mental health factor data, skin status factor data, weather-related environmental factor data, and an observed atopic dermatitis severity index based on a medical record of the patient, wherein the collecting comprises:

receiving the daily life factor data, the mental health factor data, and the skin status factor data from a user terminal associated with the patient, the user terminal executing a mobile application for atopic dermatitis management, receiving the biometric factor data and the observed atopic dermatitis severity index from a hospital server storing medical information of the patient, and receiving the weather-related environmental factor data from a weather server providing location-based weather information in response to location information comprising a global positioning system location of the user terminal, wherein the weather-related environmental factor data comprises one or more of humidity, temperature, fine dust, pollen concentration risk index, ultraviolet index, asthma index, and heat index;

storing the patient data collected on an hourly basis as time-series data for a plurality of patients;

training a learning model using the time-series data, the learning model configured to output an estimated atopic dermatitis severity index as a weighted sum of a plurality of variables and an error term representing a residual error between the estimated atopic dermatitis severity index and the observed atopic dermatitis severity index, wherein the plurality of variables comprises thirty variables including variables for each factor of a plurality of factors comprising a daily life factor, a biometric factor, a mental health factor, a skin status factor, and a weather-related environmental factor, wherein the training comprises iteratively adjusting a weight coefficient for each variable until the residual error falls below an error threshold;

determining for each factor, a threshold weight value selected to cause at least N variables for the factor to have respective weight coefficients greater than or equal to the threshold weight value, N being an integer greater than or equal to two;

reconstructing the learning model by selecting for each factor, variables having respective weight coefficients greater than or equal to the threshold weight value and excluding variables having weight coefficients less than the threshold weight value, wherein the reconstructing reduces the number of variables used by the learning model from thirty to a reduced number of variables that is fewer than thirty to increase computational efficiency and processing speed of a processor that executes the reconstructed learning model;

relearning the reconstructed learning model by applying the selected variables and the observed atopic dermatitis severity index to the reconstructed learning model;

predicting a future atopic dermatitis severity index by applying the patient data collected for the patient at a current time to the reconstructed learning model; and providing a plurality of educational content through the mobile application on the user terminal in response to receiving the patient data from the patient, the plurality of educational content being provided in a stepwise sequence comprising cognitive correction content, automatic thought improvement content, and behavior correction content, wherein, the cognitive correction content comprises an educational program that provides educational information about atopic dermatitis to correct a false perception of atopic dermatitis by the patient during a first set period, the automatic thought improvement content comprises an educational program that is provided during a second set period after completion of the cognitive correction content, the program providing training to reduce negative thinking that negatively affects daily life and disease progression based on questionnaires and responses presented to the patient, and the behavior correction content comprises an educational program that is provided during a third set period after completion of the automatic thought improvement content, the program providing meditation education and training for mindfulness of the patient.

2. The method of claim 1, wherein the training comprises applying variable values for each factor collected for the patient at a first time, and the observed atopic dermatitis severity index collected for the patient at a second time after a duration T1 has elapsed from the first time, to the learning model.

3. The method of claim 2, wherein the predicting comprises applying the selected variables for each factor from the patient data collected for the patient at a current time to the reconstructed learning model to predict the future atopic dermatitis severity index for the patient at a future time after the duration T1 has elapsed from the current time.

4. The method of claim 1, further comprising feeding back, to the user terminal associated with the patient, the future atopic dermatitis severity index and a treatment strategy selected fromfor a customized topical application, a maintenance therapy, and a recommendation to visit a hospital, wherein the treatment strategy corresponds to the future atopic dermatitis severity index.

5. An apparatus for managing atopic dermatitis, the apparatus comprising:

one or more units being configured and executed by a processor using an algorithm, the algorithm which when executed, causing the processor to perform the one or more units, the one or more units comprising:

a data collection unit configured to collect, on an hourly basis, patient data for a patient, the patient data comprising daily life factor data, biometric factor data, mental health factor data, skin status factor data, weather-related environmental factor data, and an observed atopic dermatitis severity index based on a medical record of the patient wherein the data collection unit is configured to:

receive the daily life factor data, the mental health factor data, and the skin status factor data from a user terminal associated with the patient, the user terminal configured to execute a mobile application for atopic dermatitis management;

receive the biometric factor data and the observed atopic dermatitis severity index from a hospital server storing medical information of the patient; and receive the weather-related environmental factor data from a weather server providing location-based weather information in response to location information received from the user terminal, the location information comprising a global positioning system location of the user terminal, wherein the weather-related environmental factor data comprises one or more of humidity, temperature, fine dust, pollen concentration risk index, ultraviolet index, asthma index, and heat index;

a model learning unit configured to train a learning model using time-series data formed from patient data collected on an hourly basis for a plurality of patients, the learning model configured to output an estimated atopic dermatitis severity index as a weighted sum of a plurality of variables and an error term representing a residual error between the estimated atopic dermatitis severity index and the observed atopic dermatitis severity index, wherein the plurality of variables comprises thirty variables including variables for each factor of a plurality of factors comprising a daily life factor, a biometric factor, a mental health factor, a skin status factor, and a weather-related environmental factor, wherein the model learning unit is configured to iteratively adjust a weight coefficient for each variables until the residual error falls below an error threshold;

a determination unit configured to determine, for each factor, a threshold weight value selected to cause at least N variables for the factor to have respective weight coefficients greater than or equal to the threshold weight value, N being an integer greater than or equal to two;

a model reconstruction unit configured to reconstruct the learning model by selecting, for each factor, variables having respective weight coefficients greater than or equal to the threshold weight value and excluding variables having weight coefficients less than the threshold weight value, wherein the model reconstruction unit is configured to reduce the number of variables used by the learning model from thirty to a reduced number of variables that is fewer than thirty to increase computational efficiency and processing speed of the processor that executes the reconstructed learning model, wherein the model learning unit is further configured to relearn the reconstructed learning model by applying the selected variables and the observed atopic dermatitis severity index to the reconstructed learning model;

a prediction unit configured to predict a future atopic dermatitis severity index by applying the patient data collected for the patient at a current time to the reconstructed learning model; and a content providing unit configured to provide a plurality of educational content through the mobile application on the user terminal in response to receiving the patient data from the patient, the plurality of educational content being provided in a stepwise sequence comprising cognitive correction content, automatic through improvement content, and behavior correction content, wherein, the cognitive correction content comprises an educational program that provides educational information about atopic dermatitis to correct a false perception of atopic dermatitis of the patient during a first set period, the automatic thought improvement content comprises an educational program that is provided during a second set period after completion of the cognitive correction content and that provides training to reduce negative thinking that negatively affects daily life and disease progression based on questionnaires and responses presented to the patient, and the behavior correction content comprises an educational program that is provided during a third set period after completion of the automatic thought improvement content and that provides meditation education and training for mindfulness of the patient.

6. The apparatus of claim 5, wherein the model learning unit is configured to train the learning model by applying variable values for each factor collected for the patient at a first time, and the observed atopic dermatitis severity index collected for the patient at a second time after a duration T1 has elapsed from the first time to the learning model.

7. The apparatus of claim 6, wherein the prediction unit is configured to apply the selected variables for each factor from the patient data collected for the patient at a current time to the reconstructed learning model to predict the future atopic dermatitis severity index for the patient at a future time after the duration T1 has elapsed from the current time.

8. The apparatus of claim 5, further comprising an alarm unit configured to feed back, to the user terminal associated with the patient, the future atopic dermatitis severity index and a treatment strategy selected from a customized topical application, a maintenance therapy, and a recommendation to visit a hospital, wherein the treatment strategy corresponds to the future atopic dermatitis severity index.

* * * * *